(12) United States Patent
Skutnik

(10) Patent No.: US 6,810,184 B2
(45) Date of Patent: Oct. 26, 2004

(54) DEVICE AND METHOD TO SCATTER OPTICAL FIBER OUTPUT

(75) Inventor: Bolesh J. Skutnik, West Hartford, CT (US)

(73) Assignee: Ceram Optec Industries Inc., East Longmeadow, MA (US)

(*) Notice: Subject to any disclaimer, the term of this patent is extended or adjusted under 35 U.S.C. 154(b) by 0 days.

(21) Appl. No.: 10/042,976

(22) Filed: Jan. 9, 2002

(65) Prior Publication Data

US 2003/0128944 A1 Jul. 10, 2003

(51) Int. Cl.[7] ............................. G02B 6/16; G02B 6/18; G02B 6/26
(52) U.S. Cl. ............................. 385/123; 385/31; 385/39; 385/43; 385/124
(58) Field of Search ........................ 606/15, 16; 385/31, 385/39, 43, 123–128, 901

(56) References Cited

U.S. PATENT DOCUMENTS

| | | | |
|---|---|---|---|
| 3,272,646 A | | 9/1966 | Chopoorian et al. |
| 3,938,974 A | | 2/1976 | Macedo et al. |
| 4,236,930 A | | 12/1980 | Macedo et al. |
| 4,665,039 A | | 5/1987 | Kokubu et al. |
| 4,678,279 A | * | 7/1987 | Mori ........................... 362/551 |
| 4,693,556 A | | 9/1987 | McCaughan |
| 4,835,057 A | | 5/1989 | Bagley et al. |
| 4,885,186 A | | 12/1989 | Bagley et al. |
| 5,074,632 A | | 12/1991 | Potter |
| 5,098,178 A | * | 3/1992 | Ortabasi ...................... 505/124 |
| 5,169,421 A | * | 12/1992 | Yagi et al. ..................... 65/401 |
| 5,250,095 A | | 10/1993 | Sigel et al. |
| 5,269,777 A | | 12/1993 | Doiron et al. |
| 5,279,633 A | * | 1/1994 | Fleming ........................ 65/395 |
| 5,292,320 A | * | 3/1994 | Brown et al. .................. 606/15 |
| 5,330,465 A | | 7/1994 | Doiron et al. |
| 5,337,381 A | | 8/1994 | Biswas et al. |
| 5,363,458 A | | 11/1994 | Pan et al. |
| 5,373,571 A | | 12/1994 | Reid et al. |
| 5,429,635 A | | 7/1995 | Purcell et al. |
| 5,431,647 A | | 7/1995 | Purcell et al. |
| 5,671,314 A | | 9/1997 | Gregory et al. |
| 5,684,907 A | * | 11/1997 | Sprehn et al. ............... 385/123 |
| 5,747,348 A | * | 5/1998 | Jaduszliwer et al. ........ 436/106 |
| 5,754,717 A | | 5/1998 | Esch |
| 5,807,607 A | * | 9/1998 | Smith et al. ................. 438/758 |

(List continued on next page.)

FOREIGN PATENT DOCUMENTS

| | | | | |
|---|---|---|---|---|
| JP | 11-84136 | * | 3/1999 | ............ G02B/6/00 |
| JP | 2000-137119 | * | 5/2000 | ............ G02B/6/00 |

OTHER PUBLICATIONS

Dawnay, Fardad, Green, and Yeatman "Growth and characterization of semiconductor nanoparticles in porous sol–gel films", J. Mater. Res. Materials Research Society, vol. 12, No. 11, 1997, pp. 3115–3126.*

*Primary Examiner*—John D. Lee
(74) *Attorney, Agent, or Firm*—Bolesh J. Skutnik; B J Associates

(57) ABSTRACT

The present invention provides improved diffusion tips for optical fibers and methods of making the same. Nanoporous silica clad optical fibers are used to make fibers having integrally formed diffusion tips and diffusion tips that can be fused to other fibers. The disclosed diffusers can be fabricated to be cylindrical with light diffusing along its length, spherical with light radiating outwardly in a spherical pattern, or custom shaped to illuminate irregular surfaces or volumes. Gradient and step index properties can also be achieved. Several fabrication methods to achieve the desired effects are described. The problems in the prior art methods associated with epoxy, such as curing, bond strength, embrittlement, power handling limitations, and refractive index matching are avoided.

13 Claims, 2 Drawing Sheets

OTHER PUBLICATIONS 5,922,299 A * 7/1999 Bruinsma et al. ............ 423/335
5,923,694 A * 7/1999 Culver ........................ 372/69
5,976,175 A    11/1999 Hirano et al.
5,978,541 A    11/1999 Doiron et al.
6,124,191 A * 9/2000 Bohr .......................... 438/595
6,154,595 A * 11/2000 Yokogawa et al. ......... 385/127
6,270,492 B1    8/2001 Sinosfsky
6,469,390 B2 * 10/2002 Chang et al. ............... 257/758
2002/0152771 A1 * 10/2002 Bhandarkar et al. .......... 65/395

* cited by examiner

DEVICE AND METHOD TO SCATTER OPTICAL FIBER OUTPUT

BACKGROUND OF THE INVENTION

1. Field of the Invention

This invention relates to a device and method to diffuse light from the distal end of an optical fiber.

2. Information Disclosure Statement

The radiation emitted by a laser beam source can be coupled into an optical fiber of suitable dimensions and optical properties wherein the light can be transported with no significant losses over very long distances. Today's state of the art fibers have found broad application in the fields of telecommunication, optical inspection, medical therapy, laser applications and many more. The fabrication processes are well understood and optical fibers are manufactured in large quantities, having high quality and long lifetimes.

Optical fibers rely on total internal reflection at the interface between the fiber core and the surrounding cladding to contain the light within the core of the fiber. The light guiding effect occurs in optical fibers where cores are much larger than the wavelength of the incident light. For light guiding to occur, the refractive index of the fiber cladding must be lower than the refractive index of the fiber core. A light ray incident to the fiber core's end under an angle sufficiently small relative to the fiber axis can enter the fiber and is refracted according Snell's law into a certain angle. It then hits the interface between fiber core and cladding and is, assuming the angle of incidence to the surface is sufficiently large, totally reflected back into the core. If no bends occur that exceed a critical curvature, the light cannot leave the fiber core and is thus guided through the fiber until it reaches the end.

There are a number of medical and technical applications that require some means to diffuse the light from the distal end of an optical fiber. Photodynamic therapy, deposition of thermal energy, special illumination and irradiation are prime uses. Diffusion sites on optical fiber have also found uses as optical sensors. Most often, special fiber optic tips are prepared to realize these functions.

There are several general methods for producing diffusing tips for optical fiber. The simplest is removing a section of cladding from an optical fiber then coating the bare core with a layer of optical scattering materials. Another would be to physically change the core or cladding by roughing their surfaces. Light scattering elements may also be introduced into the core or cladding to enhance scattering at desired locations, but this typically must be done by adding scattering materials at the time the fibers is drawn or by causing physical defects in the core or cladding post production. Any mechanical processes used to manufacture such diffusion sites inherently weaken the optical fiber.

The most common means to achieve light distribution from optical fibers are specially fabricated diffusion tips that are joined to the distal end of an optical fiber. These diffusers are frequently threaded onto the end of the optical fiber or glued on with an optical adhesive. These techniques require skilled persons to fabricate and assemble these probes. Misalignment or mishandling of the fiber end during manufacturing or use gives rise to concerns about whether the mechanical reliability and strength of the fiber has been compromised in the critical distal end. This is especially true with small fiber diameters. A selection of patents is presented to demonstrate the details associated with cylindrical diffusers.

U.S. Pat. No. 5,074,632 discloses a fiber optic cylindrical diffuser which includes a fiber with a jacket stripped core tip, a thin layer of scattering medium coated on the bare core tip and a sleeve member that encloses the fiber tip without touching the scattering medium. The scattering medium is a filled optical adhesive and the sleeve member threads onto the fiber jacket.

U.S. Pat. No. 5,337,381 discloses a cylindrical light diffuser where an exposed fiber core end has a conical shape. The core end is enclosed by a sleeve having a conical end, which is filled with a light diffusing polymeric material, and threaded onto the fiber sheath. Also disclosed is shaping of the exposed core into a stepped conical or undulating shape to permit greater uniformity in near and far field illumination.

U.S. Pat. No. 5,363,458 discloses a cylindrical diffuser which improves on U.S. Pat. No. 5,337,381 by including rings of prescribed indices of refraction about the unclad distal end of the fiber. One or more rings of low index of refraction material permit the tailoring of the emission profile.

U.S. Pat. No. 5,373,571 discloses a fiber optic diffusing tip having an unclad stripped terminal end of the optical fiber that is inwardly tapered towards its end such that light scattering epoxy media disposed between a glass tube and the unclad end provides a predictable light distribution. A mirrored end face is disclosed to reduce hot spots. Scattering particles size is used to center the core in the tube.

U.S. Pat. No. 5,431,647 describes a fiber optic diffuser comprising a transparent resin cylindrical cap and a polyester diffusing sleeve disposed about an exposed core. The diffuser is internally threaded and secured to a buffer layer surrounding the fiber with that aid of a wicking adhesive. A reflector is incorporated to reflect light rays exiting the end the core. The described diffuser would be expensive to manufacture due to its complex design. Due to the cap structure, the length of the diffusion area is limited.

U.S. Pat. No. 5,754,717 discloses a diffusing tip surrounding having an inner core and an outer covering, where the interior surface of the outer covering is modified such that light transmitting down the fiber is removed from the core upon encountering the modifications. The core material is preferably transparent silicone and the covering material a fluoropolymer. A scattering portion prevents formation of a hot spot and the distal end of the tip. The index of refraction of silicone is temperature sensitive, decreasing as the temperature increases.

Cylindrical diffusers have technological limits. Optical fibers are weakened by any mechanical processing. Cylinder diffusers are often inflexible, having glass or plastic outer shells. The greatest hindrance may be the materials used, such as epoxy adhesives, plastics shells and connectors, and silicone fillers that may limit the power the device can support and maintain. Under high laser intensities, hard plastics such as polymethylmethacrylate resin and polystyrene resin, and some softer plastics, like polyethylene resin, experience a blackening phenomenon due to the generation of free carbon that deteriorates light irradiating performance.

Closely related to the cylindrical diffusers are spherical diffusers, which produce illumination essentially in a spherical pattern.

U.S. Pat. No. 4,693,556 discloses an optical radiator that produces a spherical pattern of light. A short exposed core from an optical fiber is dipped into a scattering medium composed of powdered quartz and an optical adhesive. The medium is shaped into a spherical pattern then cured. The diffuser may have a uniform output, but would be impractical to manufacture on a large scale.

U.S. Pat. No. 5,429,635 discloses a fiber optic diffuser for photodynamic therapy comprising a core with an exposed distal end having a conical configuration, which is covered by a cap comprised of polycarbonate and a light scattering material, having a cavity filled with air or a substantially transparent material having a low index of refraction surrounding the fiber core. The cap is threadably attached to a buffer layer on the fiber with a wicking adhesive. This would be difficult to manufacture and the materials would limit the application environments.

A newer class of optical diffusers involves the use of elastomers.

U.S. Pat. No. 5,269,777 discloses a diffusion tip for an optical fiber comprising a silicone core abutted to the end of a conventional optical fiber, an outer layer of silicone plus a scatterer, and a final "cladding" of plastic tubing.

U.S. Pat. No. 5,330,465 discloses a continuous gradient diffuser tip having a cylindrical center core of transparent elastomer that contains embedded scattering centers. The scattering centers have a concentration that continuously increases towards the distal end of the diffuser. The use of an air space disposed between the tip of the optical fiber core and the core of the diffuser to reduce power density is presented.

U.S. Pat. No. 5,978,541 discloses a custom cylindrical diffusion tip having scattering centers embedded in a transparent elastomeric core. Distributions of scattering centers in the diffuser tip axial to the direction of the optical fiber, exponential distribution of centers along the diffuser length to produce an even illumination along the diffuser, and custom patterns of scattering centers to provide illumination of irregular cavities are discussed. A modular diffuser tip from a plurality of core plugs having particular concentrations of scatters is also presented.

Due to the limitations of the elastomer materials, these types of diffusers may be even more susceptible to failure under high power radiation than the previously described cylindrical diffusers.

Specialized diffusers, which involved highly complicated fabrication techniques or specialty materials are also known.

U.S. Pat. No. 5,671,314 discloses am illumination device for ultraviolet light different angles of incidences along the illumination window. Semi-conical, truncated conical and bi-tapered contours are discussed. An optical scattering material, preferably an admixture of optical epoxy and aluminum oxide, is formed over the fiber in the illumination window.

U.S. Pat. No. 6,270,492 discloses a light diffusing fiber tip assembly having a scattering medium and reflective end cap that provides as substantially uniform axial distribution of radiation. Silicone, epoxy or polymeric materials are listed. Described is a dielectric reflector structure that is operatively coupled to the phototherapeutic instrument to reflect light without substantial heating. Liquid-filled scattering assemblies, laminate scattering tubes formed from multiple layers, longitudinal reflectors, and the use of a bundle of optical fibers into a common diffusive tip are disclosed.

U.S. Pat. No. 5,976,175 disclose a fiber optic conducting probe having an end tip made of polyamide resin. The tips can be manufactured by a cutting process from a stock block or by molding and slow cooling a molten material. The tips do not become thermally softened or expanded when exposed to laser intensity of 8 mJ/pulse or at a frequency of 80 Hz or more. Diffusion tips are threaded and fixed to a fiber jacket by epoxy resin.

These specialty diffusers are very complicated to manufacture and additionally have the limitations associated with epoxy and polymers.

Most prior art diffusion elements involve an attachment of a dissimilar material to the end of an optical fiber or controlled damage to the fiber core or cladding. In most prior art diffusers, epoxy is used as an adhesive to attach the diffuser to the optical fiber or as a major component of the diffuser in which a scattering material is blended. If the index of refraction of the epoxy does not match that of the fiber core, refractive loss at the core/epoxy interface will result.

Another issue with epoxy is curing conditions. If sufficient curing time and temperature are not provided, the bond will not be reliable. Moisture, surface roughness, internal bubbles and contamination at the interface will also affect the bond obtained. Even when curing conditions are believed to be adequate, it is difficult to ascertain that the bond is fully cured. In diffusers produced by repetitive coat/cure layering of an epoxy/scatterer mixture, improper curing can lead to delamination of the diffuser. Still another problem with epoxy is embrittlement. When exposed to high energy for long periods, the probability of epoxy embrittlement is increased, and subsequent cracking will eventually lead to failure A solution to the problems of current optical fiber diffusers may be found in the technology for the production of porous glass. The use of porous glass to form objects and fibers is known.

U.S. Pat. No. 4,665,039 describes a process for producing a porous glass and a heat treatment to induce phase separation and subsequent leaching to produce a porous glass form.

U.S. Pat. No. 3,938,974 describes a method of producing an optical waveguide fiber from a phase-separable glass. A soluble phase is leached out to form a porous glass. The pores are collapsed and the glass is used to make cores and/or cladding layers. In one aspect, precursors of the porous glass have their interconnected pores stuffed with a dopant, which modifies the index of refraction. Dopant may be non-uniformly deposited in order to produce a radial gradient in the index of refraction U.S. Pat. No. 5,250,095 describes a method for making porous glass optical fiber sensor. Described is a glass optical fiber having a surface of interconnected and permeable chambers within the fiber. The method of producing this fiber includes heating the fiber to induce phase separation and a leaching phase. An indicator can be applied to the surface for sensing. The sensor is used in conjunction with a light source, light detector, and means for measuring change in the light caused by an agent within the porosity of the sensor.

U.S. Pat. No. 3,272,646 disclosed an impregnated porous photochromic glass having pores that are impregnated with a solution that darkens in the presence of ultraviolet light. The patent also teaches entrapping the acid in the pores by coating the porous member with a film.

U.S. Pat. No. 4,236,930 discloses an optical waveguide produced by locating a dopant within the porosity of a glass form, collapsing the form, and producing an optical fiber.

U.S. Pat. No. 4,835,057 discloses glass fibers having organosilsesquioxane coatings and claddings. The polymer serves as a cladding or coating for silica-based fibers, and as a water barrier in humid environments. The polymeric material is applied to a conventional silica or silica based fiber by heating the polymer to a desired viscosity and drawing the fiber through a die coating cup containing the polymer. In an alternative technique the desired viscosity of the organosilsesquioxane polymer is obtained by means of an organic solvent rather than heating. Following the coat, the fiber is drawn through a furnace to effect curing at about 150–400° C. The result is an organosilicon polymeric cladding. No further modification of the fiber to produce optical diffusers is discussed.

U.S. Pat. No. 4,885,186 discloses a method for preparing silicate glasses of controlled index of refraction by thermal or plasma processing of organo-silicon polymers. The compositions evidence a suppressed index of refraction, which may be subsequently increased by sintering at 1000–1100° C. Discussed is the production of phospho, germano and boro-silicate glasses by adding suitable sources to the organosilicon polymer. Neither the use of sintered organo-silicon polymers to form optical diffusers, nor the inclusion of scattering materials to form gradient diffusers is discussed.

The present invention builds on the teachings of porous glass technology to address the need for an optical fiber diffuser that is integral to a transmission fiber and that overcomes the problems associated with epoxy adhesives and polymeric components. There is no requirement for leaching of phase-separated materials as taught in earlier porous glass patents. The present invention avoids the need to use expensive dopants such as phosphorous, germanium and boron.

OBJECTIVES AND BRIEF SUMMARY OF THE INVENTION

An object of the present invention is to provide a diffuser that can be integrated into an optical fiber.

Another object of the present invention is to provide a method of manufacturing a diffuser that minimizes the chance of optical, thermal or mechanical damage during use.

Still another object of the present invention to provide an improved optical diffuser for the distal end of an optical fiber that decreases time and cost factors associated with its manufacture.

Yet another object of the present invention to provide a diffuser for an optical fiber based on sol/gel technology.

A further object of the present invention optical fiber diffusion tip for use in photodynamic therapy that has a diameter no larger than that of the optical fiber cladding.

Another object of the present invention is to provide a cylindrical diffusion tip that is flexible.

Another object of the present invention is to provide a method to produce custom shaped diffusion tips for optical fibers.

Briefly stated, the present invention provides improved diffusion tips for optical fibers and methods of making the same. Nanoporous silica clad optical fibers are used to make fibers having integrally formed diffusion tips and diffusion tips that can be fused to other fibers. The disclosed diffusers can be fabricated to be cylindrical with light diffusing along its length, spherical with light radiating outwardly in a spherical pattern, or custom shaped to illuminate irregular surfaces or volumes. Gradient and step index properties can also be achieved. Several fabrication methods to achieve the desired effects are described. The problems in the prior art methods associated with epoxy, such as curing, bond strength, embrittlement, power handling limitations, and refractive index matching are avoided.

The above and other objects, features and advantages of the present invention will become apparent from the following description read in conjunction with the accompanying drawings, (in which like reference numbers in different drawings designate the same elements.)

DETAILED DESCRIPTION OF PREFERRED EMBODIMENTS

Figure 1:
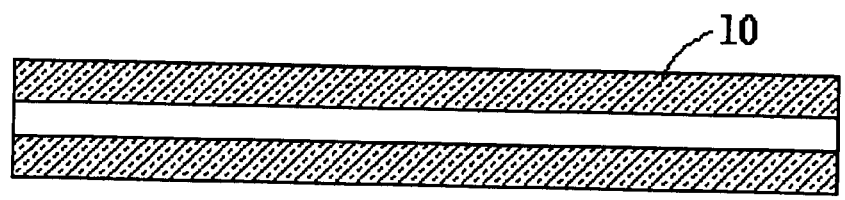
FIG. 1 is a longitudinal cross sectional view of a nanoporous silica clad optical fiber.

Optical fiber made by a modified sol-gel process results in a glass that has lesser density than bulk glass. Modified sol-gel glass is an optically transparent amorphous silica produced by forming interconnections in a polymeric network of organosilicon. A cladding produced by heating such a material is a porous glass matrix. The porosity in the sol-gel processed silica is what creates the difference in index of refraction between the core and cladding. The pores in the cladding lower the effective refractive index of the glass and enables light to be trapped in the core of the fiber.

The diffusing tips of the present invention are produced from nanoporous silica claddings produced from a modified sol-gel process. The starting materials for these novel sol-gel based claddings consist of oligomeric silica precursors. A typical oligomeric precursor material is GR650F, a glass resin marketed by Techneglas Corp. in Toledo, Ohio. The flake form is a three dimensional ladder oligomer of silica functionalized with methyl groups and end capped with some OH and ethoxy groups, known as polymethylsilsequioxane. Due to the organo side groups, GR650F is highly soluble in polar organic solvents such as ethyl acetate or alcohols. A preferred solvent selected to form the sol/gel with the GR650F glass resin is ethyl acetate.

A sol-gel coating solution was made by mixing 50% by weight G650F into a preweighed amount of solvent. The mixture was then warmed and stirred until the solid resin dissolved. The coating solution was shown to be stable for at least several days and upwards of one month.

The glass cores used were composed of high purity synthetic silica with no dopants. The cores were coated with the sol-gel coating solution. A simple method of coating tips of glass cores or short lengths of glass core is simply to dip or draw through a bath containing the solution. Coating the bare core with the organosilicon polymer provides immediate protection to the core upon drying. Simply removing the solvent caused the ladder polymer molecules to coalesce into a continuous network. When exposed to a temperature of about 300° C. the solution converts to an organosilicon polymeric cladding. Solvent is driven off as the hydroxy and ethoxy groups react to create the cured prepolymer. Water and ethanol residues flash off.

When the coated cores are exposed to higher temperatures, about 450 to 550° C., the organosilicon polymer converts to a nanoporous silica cladding. The nanoporous cladding has an index of refraction lower than that of the pure silica core. Exposing the nanoporous silica cladding to higher temperatures causes the nanoporous structure to consolidate. If the nanoporous cladding is treated with a scattering material prior to consolidation, an integral diffuser is formed. The effect of the scattering sites will normally be to raise the index of refraction higher than mere consolidation of the nanoporous structure. Typical scattering compounds include diamond dust, titanium dioxide, aluminum oxide, powdered sapphire, powdered zirconia and powdered quartz.

Methods of applying scattering materials will vary, but most commonly include drawing or dipping a nanoporous silica cladding into a solution or dispersion containing the scattering material. Scattering solutions may also be brushed or sprayed on. In some cases a dry form of the scattering material may applied to the nanoporous silica cladding prior to consolidation.

The diffusers of the present invention do not cause damage to the optical core. They do not require threaded structures or epoxies to connect the diffuser to the optical fiber.

Since the diffuser is essentially silica, with little or no organic component, transmission and power handling capabilities are greater than most prior art devices, which contain epoxy, silicone, polymers, or liquid filled scattering assemblies.

The true novelty of the present invention is that the diffusers can be manufactured with cores and/or claddings made of pure silica. There is no requirement for leaching of phase-separated materials as in earlier porous glass patents.

Nanoporous silica clad fiber diffusers find a novel application as indicator probes to monitor organic solvents and acids where polymer-containing diffusers would not be suitable. Nanoporous silica clad fibers diffusers/sensors may also be used in high heat environments that would melt most polymers.

Several preferred embodiments of the present invention are presented which improve upon the prior art.

In a preferred embodiment of the present invention, an optical fiber has a nanoporous silica diffuser formed on its distal end. A diffuser precursor is formed by removing the cladding in a region at one end of an optical fiber and dipping the bare core into a modified sol-gel coating mixture. The coating is dried and the dipping procedure repeated until a desired coating thickness is achieved. The coating is then cured at about 300° C. Further heating to about 450–550° C. converts the cured coating to a nanoporous silica cladding. The nanoporous cladding is then dipped into a solution of scattering material. Repeated dipping at controlled coating lengths makes it possible to produce a diffusing tip having a gradient index over its length or step index having clearly defined refractive index regions. After the scattering solution has dried, the porous cladding is heated to consolidate the cladding and form the diffuser.

In another preferred embodiment, a radial distribution of scattering material is produced. The diffuser precursor was formed by removing the cladding at one end of an optical fiber and dipping the bare core once into a sol-gel coating mixture. The coating is cured and then converted into a nanoporous silica cladding. The diffuser precursor is then dipped into a solution of scattering material and dried. The coating and dipping procedure is repeated, with a higher or lower scattering material concentration applied in each subsequent repetition. The process is repeated until a diffuser precursor of a desired thickness is achieved. Consolidation of the nanoporous diffuser precursor results in a diffuser having the desired radial distribution of scatterers.

In another preferred embodiment, a section of modified sol-gel optical fiber (FIG. 1) is cut from a longer sample that has an unconsolidated nanoporous sol-gel cladding (10). The sol-gel optical fiber is cleaved into small sections using a diamond blade cleaver. The cut sample is immersed in a fluid containing scattering particles, which can be absorbed into the nanoporous cladding. Solvent or dispersant is evaporated and the section is fusion spliced to the end of a standard optical fiber. As the fusion splice is completed, the nanoporous cladding is collapsed into silica, having scattering sites distributed throughout. Additional protection to the fusion area can be provided by applying a thin polyimide tube or coating around the area of the splice. The described method permits the manufacture of diffusers having a wide variety of scattering properties starting with a simple supply of nanoporous silica clad fiber. The manufacturer only needs to vary the type and amount of scattering material used.

Figure 2:
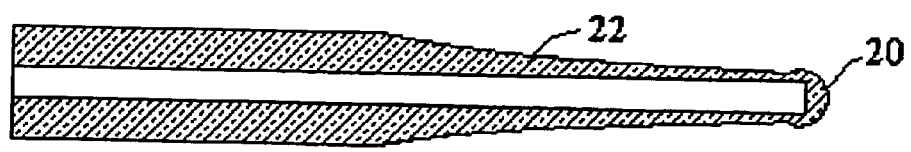
FIG. 2 is a longitudinal cross-sectional view of a nanoporous silica clad optical fiber with a section of cladding that has been consolidated into a tapered diffuser.

Another preferred embodiment of the present invention relates to cylindrical diffusers. The simple dipping of a silica core into a sol gel solution coats both the side and end of the fiber. After consolidation, the end of the fiber will diffuse light in addition to the side of the fiber. In order to prevent light from exiting the end and creating a "hot-spot" the diffuser end needs to be treated. Referring now to FIG. 2, a simple treatment is to re-dip the tip of the diffuser into the sol-gel solution and follow the procedures previously described to create an end cap (20) of nanoporous silica. Although some light may escape through the end cap, it should not create a hot spot.

Where a true cylindrical radial diffuser is required, it may be necessary to cleave the very end of the diffuser tip to create a surface normal to the direction of light propagation. The end face of the diffuser can simply be coated with a non-transmissive material such as an opaque epoxy or the end face of the fiber can be polished and coated with a reflective coating. Typically, a cerium oxide polishing compound is used. An aluminum mirror can be formed on the polished end using chemical vapor deposition or other coating techniques. The mirror will totally reflect any light reaching the distal end of the diffuser back into the diffusing region where it can diffuse radially.

Figure 3:
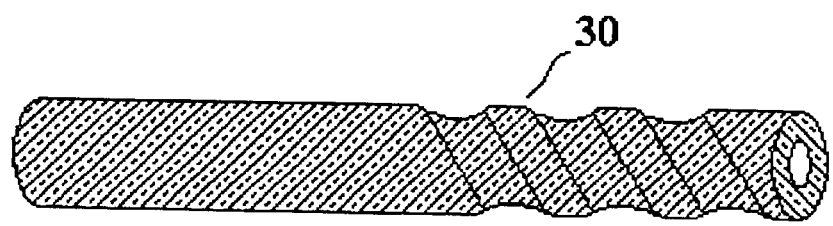
FIG. 3 illustrates a nanoporous silica clad optical fiber with a section of cladding that has been consolidated into a spiral diffuser.
Figure 4:
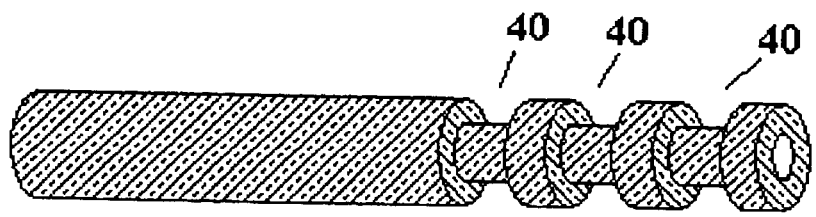
FIG. 4 illustrates a nanoporous silica clad optical fiber with a section of cladding that has been consolidated into a diffuser having a set of rings.

Consolidation of the described nanoporous silica cladding does not have to be uniform. The nanoporous cladding can be consolidated in a variety of patterns, which might better suite a specific need. Referring now to FIGS. 2, 3 and 4, consolidation can form a tapered diffusion site (22), form spiral patterns along the length of the diffuser, or form rings (40) along the length of the active section where loss is desired.

If the optical fiber used has a nanoporous silica cladding, there is no need to strip the cladding from the core. The cladding and diffuser material will be nearly identical and a subsequent buildup presents no incompatibility problems. The fibers also provide a surface that can be safely handled by the technician during assembly of the diffuser. Nanoporous silica claddings are craze resistant and any subtle damage to the surface of the cladding will not cause diffusion sites.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. The optical fiber diffuser comprising an optical fiber having a light transmitting core and a nanoporous silica cladding, wherein a section of said nanoporous cladding is modified to create scattering sites, and wherein said modification of said section of said nanoporous silica cladding is at least partially consolidating said section at a distal end of said optical fiber by heat energy.

2. The optical fiber diffuser according to claim 1, wherein said modification of said section of said nanoporous silica cladding is treating said cladding section with a light scattering compound.

3. The optical fiber diffuser according to claim 2, wherein said light scattering compound is selected from a group consisting of titanium dioxide, aluminum oxide, diamond dust, powdered sapphire, powdered zirconia and powdered quartz.

4. The optical fiber diffuser according to claim 1, wherein said nanoporous silica cladding section has been treated with a light scattering compound prior to said consolidation.

5. The optical fiber diffuser according to claim 4, wherein said a light scattering compound has a radial distribution after consolidation.

6. The optical fiber diffuser according to claim 4, wherein said diffuser has a gradient index over its length.

7. The optical fiber diffuser according to claim 4, wherein said diffuser has a step index, having clearly defined refractive index regions over its length.

8. The optical fiber diffuser according to claim 1, wherein said nanoporous silica cladding is consolidated into one or more spirals at a distal end of said optical fiber.

9. The optical fiber diffuser according to claim 1, wherein said nanoporous silica cladding is consolidated into one or more rings at a distal end of said optical fiber.

10. The optical fiber diffuser according to claim 1, wherein the shape of said diffuser is selected from a group consisting of cylindrical, elliptical, spherical, and custom shapes.

11. The optical fiber diffuser according to claim 10, having a cylindrical shape, and wherein a mirror is secured to a polished distal end of said diffuser.

12. The optical fiber diffuser according to claim 11, wherein said mirror is secured and produced by vapor deposition of a reflective metal.

13. The optical fiber diffuser according to claim 1, wherein said diffuser has a gradient index over its length.

* * * * *